United States Patent [19]
Huebsch et al.

[11] Patent Number: 6,024,756
[45] Date of Patent: *Feb. 15, 2000

[54] METHOD OF REVERSIBLY CLOSING A SEPTAL DEFECT

[75] Inventors: Joseph Huebsch, St. Paul; Paul J. Buscemi, Long Lake; Thomas J. Holman, Minneapolis; Danney Langanki, Lino Lakes, all of Minn.

[73] Assignee: SciMed Life Systems, Inc., Maple Grove, Minn.

[ * ] Notice: This patent is subject to a terminal disclaimer.

[21] Appl. No.: 09/218,380

[22] Filed: Dec. 22, 1998

Related U.S. Application Data

[62] Division of application No. 08/935,524, Sep. 23, 1997, which is a continuation of application No. 08/620,286, Mar. 22, 1996, abandoned.

[51] Int. Cl.⁷ .................................................. A61B 17/08
[52] U.S. Cl. ......................... 606/213; 606/215; 606/217
[58] Field of Search ..................................... 606/213, 215, 606/151, 157; 128/899

[56] References Cited

U.S. PATENT DOCUMENTS

| | | |
|---|---|---|
| 3,874,388 | 4/1975 | King et al. . |
| 4,007,743 | 2/1977 | Blake . |
| 4,699,611 | 10/1987 | Bowden . |
| 4,710,192 | 12/1987 | Liotta et al. . |
| 4,836,204 | 6/1989 | Landymore et al. . |
| 4,917,089 | 4/1990 | Sideris . |
| 5,108,420 | 4/1992 | Marks . |
| 5,171,259 | 12/1992 | Inoue . |
| 5,192,301 | 3/1993 | Kamiya et al. . |
| 5,350,399 | 9/1994 | Eriebacher et al. . |
| 5,437,288 | 8/1995 | Schwartz et al. ........................ 128/772 |
| 5,634,936 | 6/1997 | Linden et al. ........................... 606/213 |
| 5,861,003 | 1/1999 | Lason et al. ............................ 606/213 |

FOREIGN PATENT DOCUMENTS

| | | |
|---|---|---|
| 0 541 063 A2 | 5/1993 | European Pat. Off. . |
| 676285 | 7/1979 | Russian Federation . |
| 952234 | 1/1981 | Russian Federation . |
| 1531995 A1 | 12/1989 | Russian Federation . |
| 1 509 023 | 4/1978 | United Kingdom . |
| WO93/10714 | 6/1993 | WIPO . |
| WO93/13712 | 7/1993 | WIPO . |

*Primary Examiner*—Michael Buiz
*Assistant Examiner*—Tina T. D. Pham
*Attorney, Agent, or Firm*—Vidas, Arrett & Steinkraus, P.A.

[57] ABSTRACT

A catheter delivered device to close a septal defect, the device comprising a cylindrical shaft of metal or polymeric material with concentric parallel cuts through the wall of the device which create flattened support struts. The center of the support struts move radially away from the axis in a hinge like fashion in response to the movement of the device's proximal and distal ends toward the center of the device. This movement is reversibly effected through mechanical means. The device can be coated with growth factors, mitogenic factors or other determinants which can improve tissue growth such that tissue ingrowth can occur over a period of time. The catheter itself may be an ultrasonic imaging catheter.

8 Claims, 11 Drawing Sheets

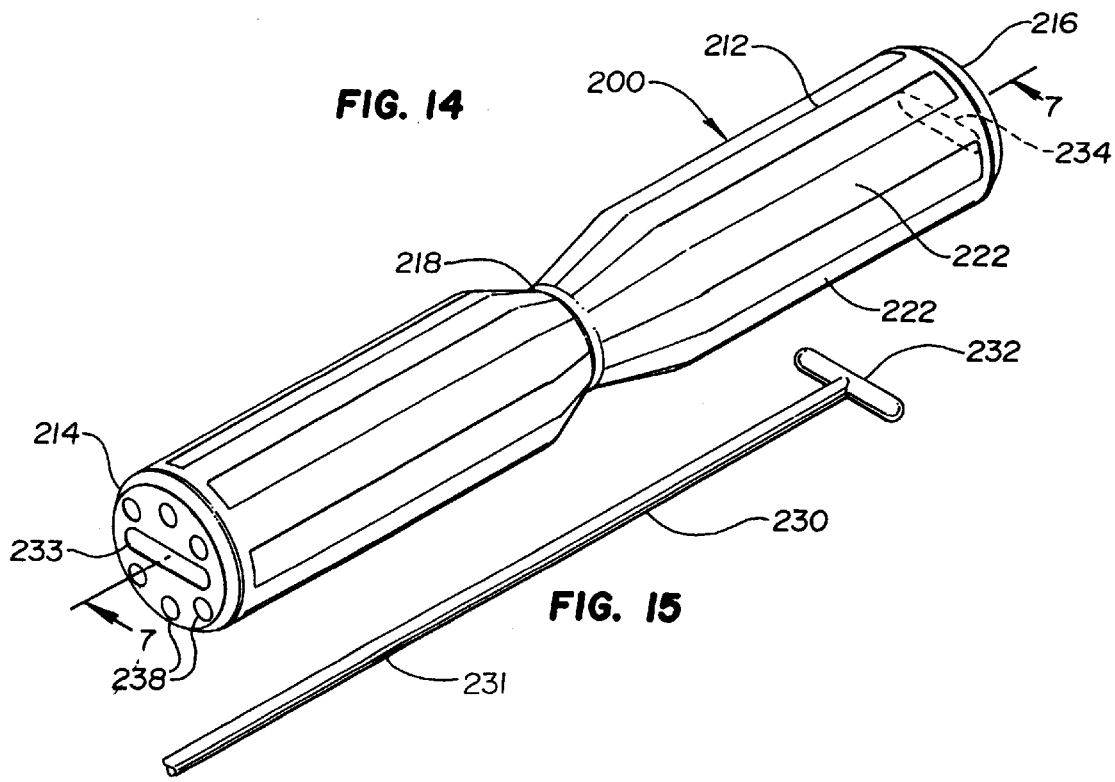
FIG. 14
FIG. 15
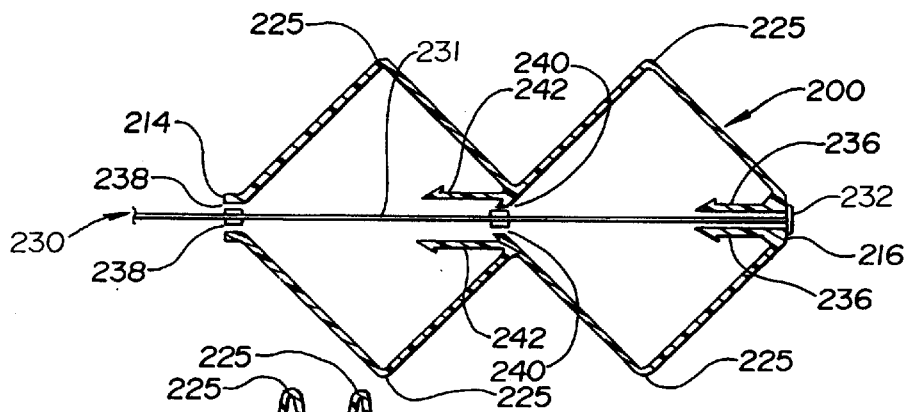
FIG. 16
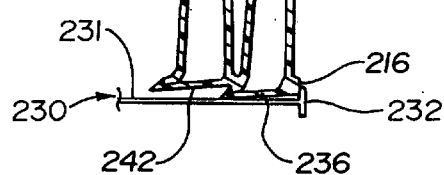
FIG. 17

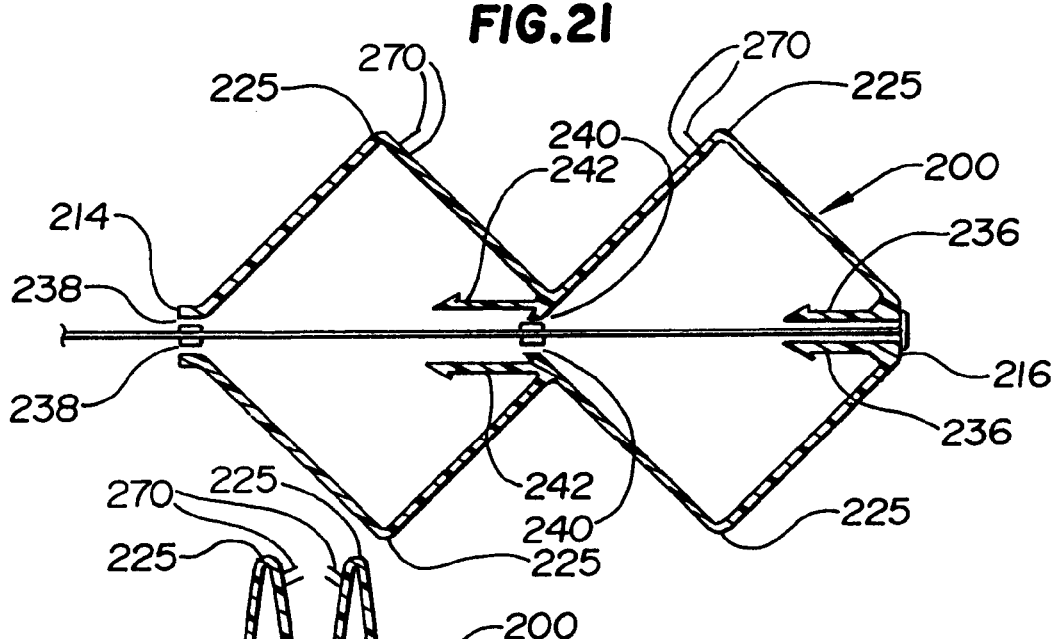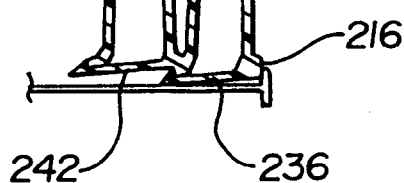

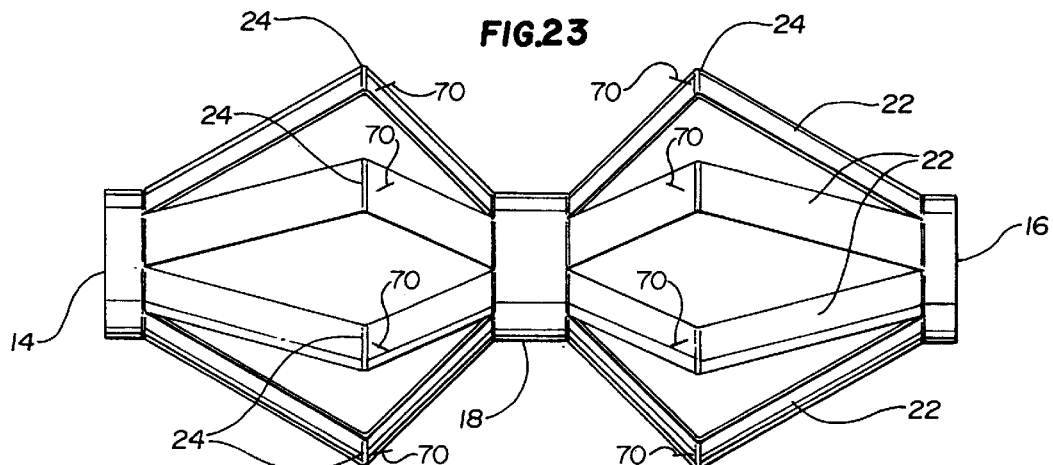
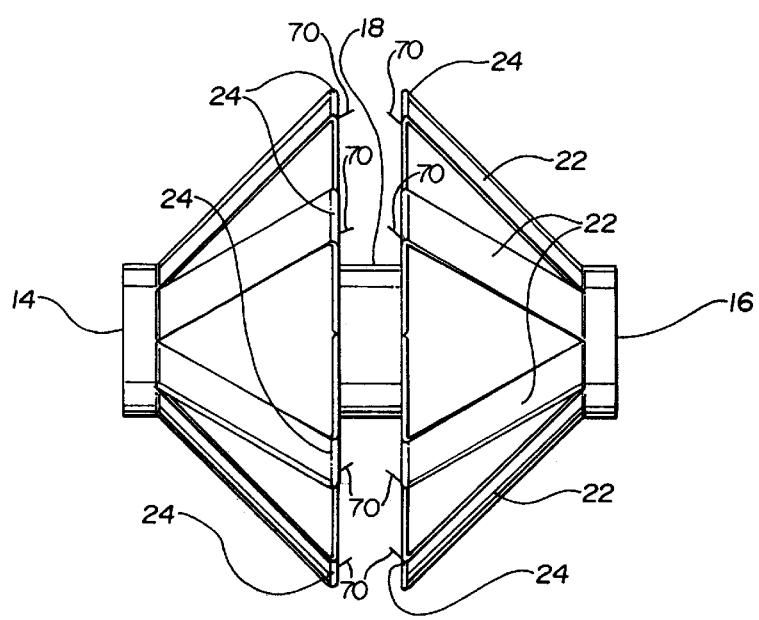

METHOD OF REVERSIBLY CLOSING A SEPTAL DEFECT

CROSS REFERENCE TO RELATED APPLICATIONS

This application is a divisional of U.S. patent application Ser. No. 08/935,524 filed Sep. 23, 1997, which is a File Wrapper Continuation of U.S. application Ser. No. 08/620,286 filed Mar. 22, 1996 (now abandoned), both of which are incorporated herein by reference.

BACKGROUND OF THE INVENTION

1. Field of the Invention

The present invention relates generally to the closure of intravascular defects and more specifically to a device for closing a septal defect, the device being delivered to the site of the defect by a catheter and comprising a metallic or polymeric material which is adjusted by mechanical means to a configuration which functions as a plug.

2. General Background

The heart is divided into four chambers, the two upper being the left and right atria and the two lower being the left and right ventricles. The atria are separated from each other by a muscular wall, the interatrial septum, and the ventricles by the interventricular septum.

Either congenitally or by acquisition, abnormal openings, holes or shunts can occur between the chambers of the heart or the great vessels (interatrial and interventricular septal defects or patent ductus arteriosus and aorthico-pulmonary window respectively), causing shunting of blood through the opening. The ductus arteriosus is the prenatal canal between the pulmonary artery and the aortic arch which normally closes soon after birth. The deformity is usually congenital, resulting from a failure of completion of the formation of the septum, or wall, between the two sides during fetal life when the heart forms from a folded tube into a four-chambered, two unit system.

These deformities can carry significant sequelae. For example, with an atrial septal defect, blood is shunted from the left atrium of the heart to the right, producing an over-load of the right heart. In addition to left-to-right shunts such as occur in patent ductus arteriosus from the aorta to the pulmonary artery, the left side of the heart has to work harder because some of the blood which it pumps will recirculate through the lungs instead of going out to the rest of the body. The ill effects of these lesions usually cause added strain on the heart with ultimate failure if not corrected.

Previous extracardiac (outside the heart) or intracardiac septal defects have required relatively extensive surgical techniques for correction. To date the most common method of closing intracardiac shunts, such as atrial-septal defects and ventricular-septal defects, entails the relatively drastic technique of open-heart surgery, requiring opening the chest or sternum and diverting the blood from the heart with the use of a cardiopulmonary bypass. The heart is then opened, the defect is sewn shut by direct suturing with or without a patch of synthetic material (usually of Dacron, teflon, silk, nylon or pericardium), and then the heart is closed. The patient is then taken off the cardiopulmonary bypass machine, and then the chest is closed.

In place of direct suturing, closures of interauricular septal defects by means of a mechanical prosthesis have been disclosed.

U.S. Pat. No. 3,874,388 to King et al. relates to a shunt defect closure system including a pair of opposed umbrella-like elements locked together in a face to face relationship and delivered by means of a catheter, whereby a defect is closed. U.S. Pat. No. 5,350,399 to Erlebacher et al. relates to a percutaneous arterial puncture seal device also including a pair of opposed umbrella-like elements and an insertion tool.

U.S. Pat. No. 4,710,192 to Liotta et al. relates to a vaulted diaphragm for occlusion in a descending thoracic aorta.

U.S. Pat. No. 5,108,420 to Marks relates to an aperture occlusion device consisting of a wire having an elongated configuration for delivery to the aperture, and a preprogrammed configuration including occlusion forming wire segments on each side of the aperture.

U.S. Pat. No. 4,007,743 to Blake relates to an opening mechanism for umbrella-like intravascular shunt defect closure device having foldable flat ring sections which extend between pivotable struts when the device is expanded and fold between the struts when the device is collapsed.

U.S. Pat. No. 4,699,611 to Bowden relates to a biliary stent having radially protruding lobes.

There still exists a need, however, for a simple mechanical method of closing septal defects, either temporarily or permanently, with an improved plug having a unitary construction that is adjusted by mechanical means from a delivery configuration to a configuration which functions as a plug at the site of a defect.

SUMMARY OF THE INVENTION

The present invention provides devices and method for closing off, restricting the blood flow through or plugging a septal defect, the devices being made of metallic or polymeric materials in specific conformations which are delivered to the area of defect by a catheter means and adjusted by mechanical means to a configuration which functions as a plug or restriction.

The device may contact both sides of the septum thereby plugging the septal defect.

The septal defect closure device of the present invention may be used to close the ductus arteriosus, ventricular septum or atrial septum, or may even be used to block or fill an artery, vein or other vessel.

The device may be in any shape which is suitable for filling and plugging a defect. The defect may be contacted by the surface of the metallic material or polymeric material, which is biocompatible.

BRIEF DESCRIPTION OF THE FIGURES

FIGS. 14–15 respectively show a perspective view of an alternative embodiment of a device according to the present invention and a pull mechanism whereby the device is transformed into a plug;

FIGS. 16–17 show a sectional view of the device of FIG. 14 including a pin locking mechanism;

FIGS. 21–22 show a sectional view of the device as in FIGS. 14, 16 and 17 further including a plurality of tissue hooks;

FIGS. 23–24 show side views of a device as shown in FIGS. 3–4 respectively, the device further including a plurality of tissue hooks, FIG. 23 showing an intermediate conformation which the device would assume after delivery and during its mechanical transformation into a plug, FIG. 24 showing a side view of the device as in FIG. 23 after its mechanical transformation into a plug;

DETAILED DESCRIPTION OF THE INVENTION

The present invention provides an apparatus and method of closing off restricting the blood flow therethrough or plugging a septal defect. The apparatus comprises a catheter delivered device to close a septal defect, the device comprising a hollow shaft with cuts or grooves in the wall of the device which create deformable hinged support struts. The shaft may have a circular cross section. The device may suitably be made of any biocompatible material. Alternatively the device could be made of a non-biocompatible material with a suitable biocompatible coating.

The device of the present invention may be made of any suitable polymeric material including but not limited to polycarbonate urethanes, polyamides, polyether urethanes, polyethylene terephthalate (PET), polybutylene terephthalate, polyethylenes, high density polyethylene, polyimides, epoxies, composites of collagen and PET, composites of high strength carbon fiber and PET and composites of PET or carbon fibers within epoxides. Any thermosets, thermoplastics, thermoplastic elastomers, elastomers, composites, pseudo-thermoplastics, carbohydrates, proteins, or mixtures thereof may suitably be used. In addition to synthetic polymers portions of the device could be constructed of natural materials as collagen I or III, or IV or of glycosaminoglycans as chondroitin sulfate or composites thereof.

The device may alternatively be made of a metallic material. Examples of suitable metallic materials include stainless steel, spring steel, memory shape metals (such as nitinol), titanium, and metal alloys of any kind not limited to the aforementioned. Furthermore, the configuration of the metal device may be solid, braided or woven.

The device may alternatively be made of carbon fiber composites coated with any of the prior cited polymeric materials or of metal fibers coated with polymeric materials. The device may be completely or partially coated with polymeric materials. The apparatus may also be comprised of metal substrates coated with polymer which is in turn coated with natural materials.

Figure 1:
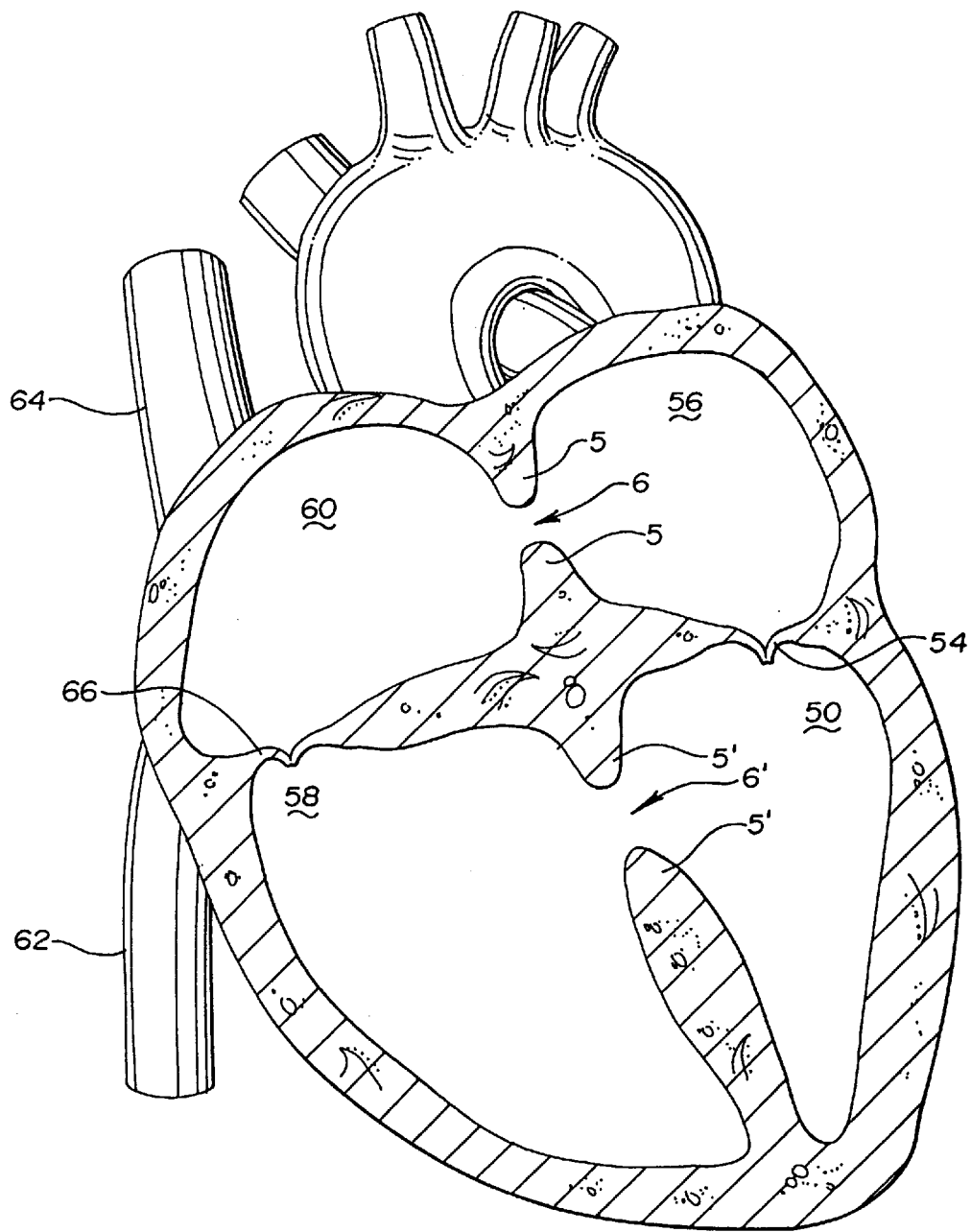
FIG. 1 shows an anterior to posterior sectional view of a human heart, showing a typical atrial septal defect (ASD) prior to closure, and a typical ventricular septal defect (VSD) prior to closure by the device of the present invention.

Referring now to the Figures, FIG. 1 is a sectional view of a human heart showing defects in septal tissue, a typical atrial septal defect (ASD) 6 and a typical ventricular septal defect (VSD) 6', prior to closure. The defects are shown together for illustrative purposes only, not as a depiction of multiple septal defects. However, multiple defects may be present. Apparent in the figure are left ventricle 50, left atrium 56, right ventricle 58, right atrium 60, mitral valve 54, tricuspid valve 66, inferior vena cava 62 and superior vena cava 64.

Figure 2:
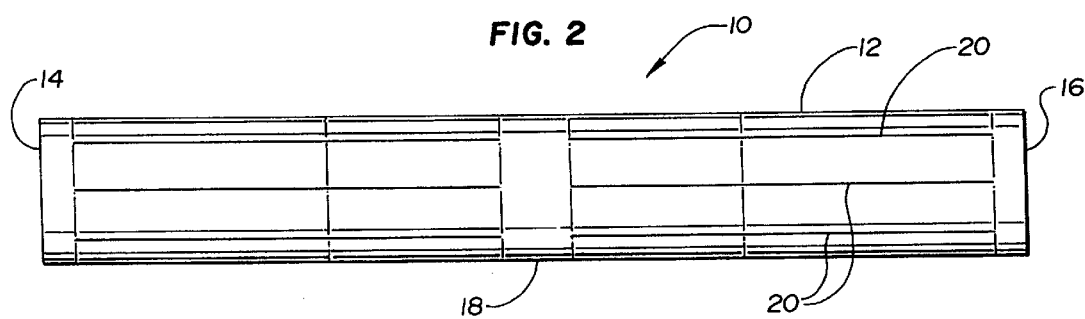
FIG. 2 shows a side view of a septal defect closure device of the present invention in its delivery state.
Figure 3:
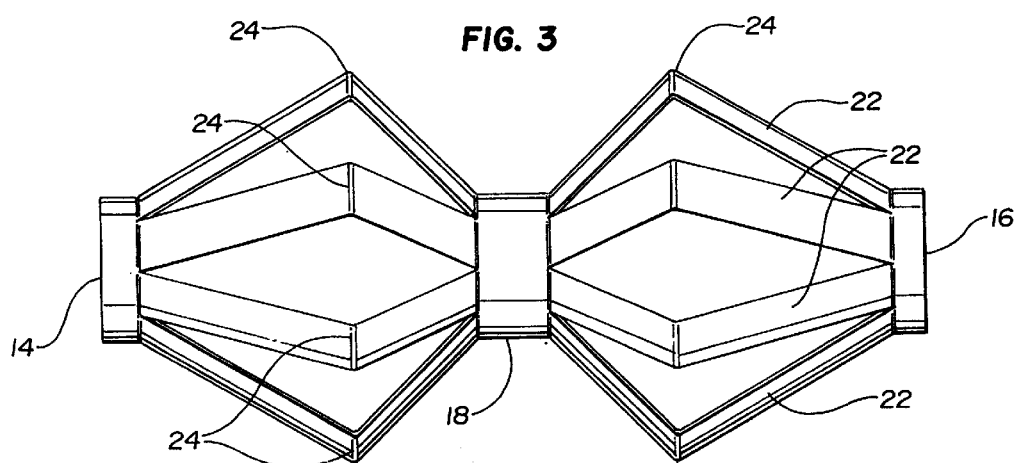
FIG. 3 is a side view of the device of FIG. 2 in an intermediate conformation which it would assume after delivery and during its mechanical transformation into a plug.
Figure 4:
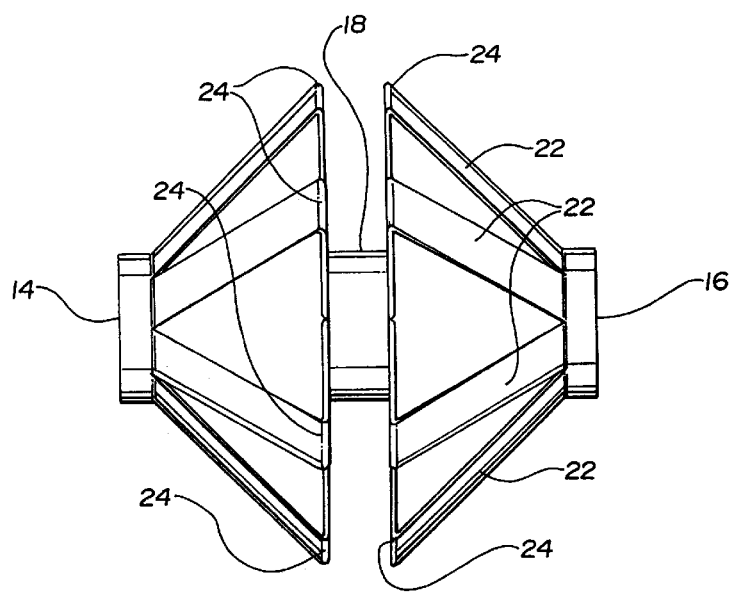
FIG. 4 is a side view of the device as in FIG. 3 after its mechanical transformation into a plug.

As shown in FIG. 2, the catheter delivered device, shown generally at 10, comprises a cylindrical shaft 12 having a proximal end 14, a distal end 16, and a central portion 18. Cylindrical shaft 12 has parallel cuts 20 therethrough, which as shown in FIGS. 3–5, create support struts 22. The cuts could also be helical or serpentine. The struts could be covered by a cloth or other covering.

As shown in FIGS. 2–4, 5a and 5b, hinge point 24 of support struts 22 move radially away from the axis of the device in a hinge like fashion in response to the movement of proximal and distal ends 14, 16 toward the central portion 18 of the device 10. The hinge point 24 could be formed in a variety of ways. It could be a mechanical hinge, a thinned section created by chemical etching, mechanical denting, grinding, heat forming or machining, a weakened section created by micro cuts, tapered grooves (20), chemical treatment, or any other process which will cause a preferential stress point.

Figure 5A:
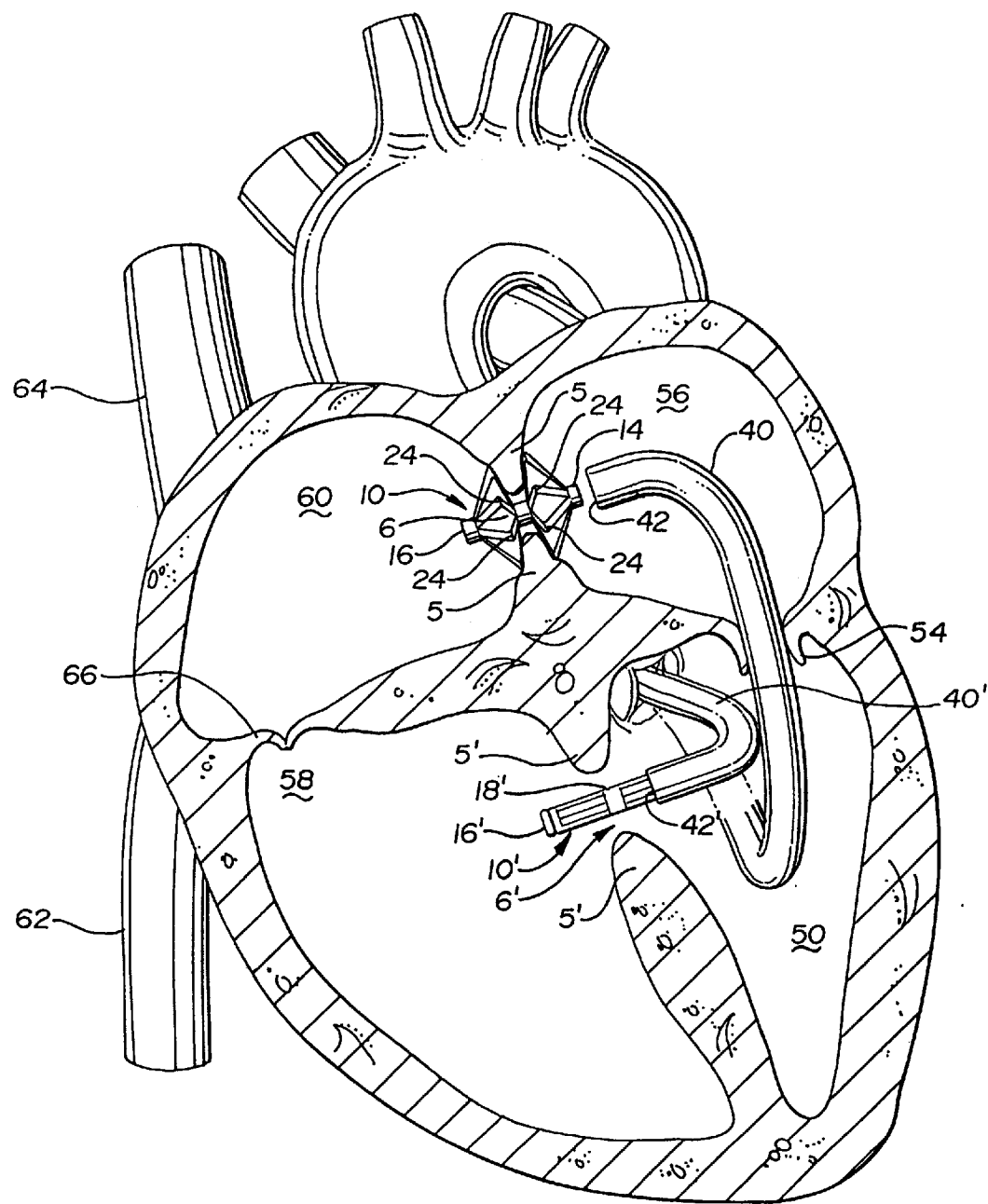
FIGS. 5a and 5b are anterior to posterior sectional views showing the delivery and placement of the septal defect closure device of FIG. 2.
Figure 5B:
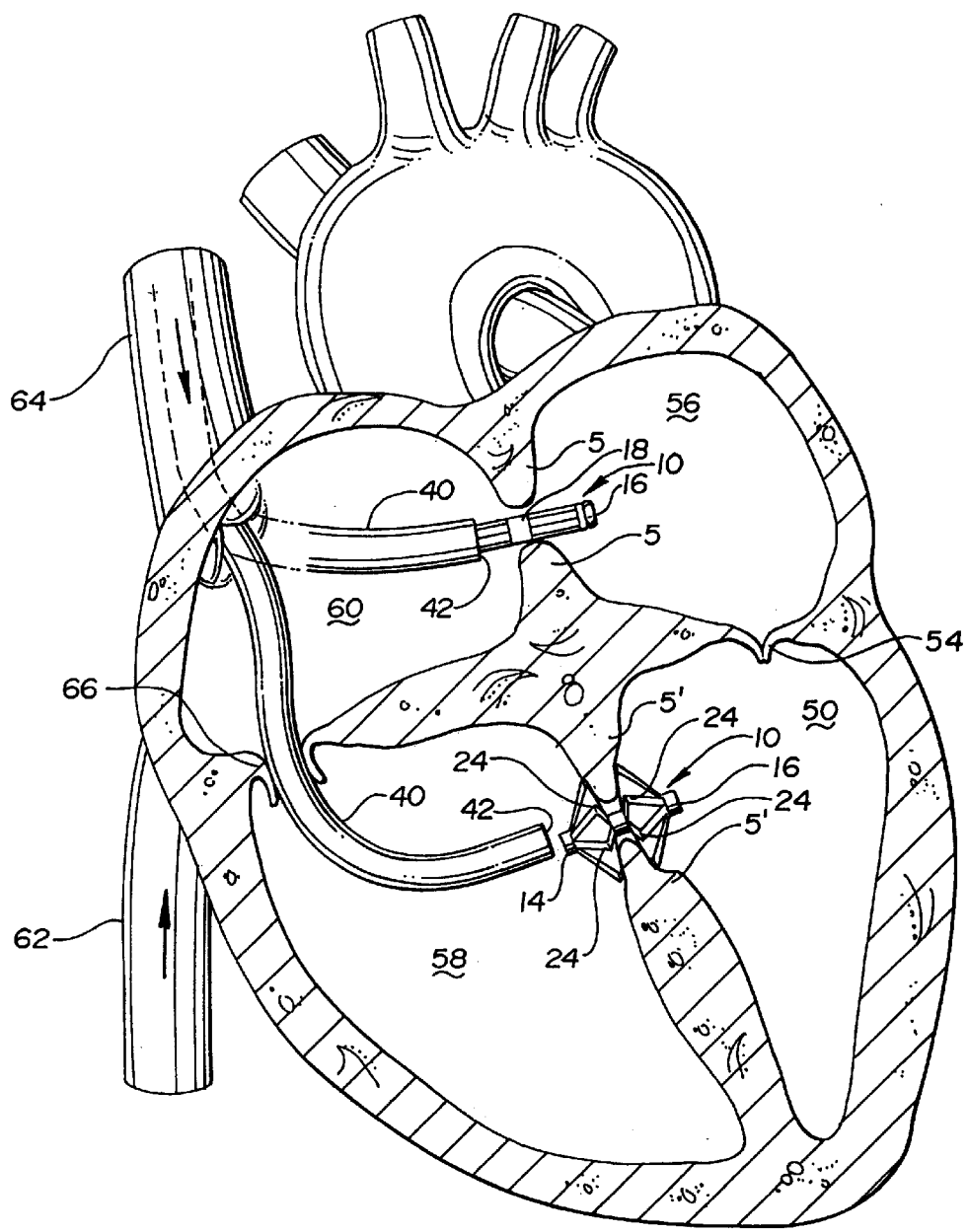

As shown in FIGS. 4, 5a and 5b, the device will assume a plug like formation when in place, whereby device 10 will span both sides of the septal defect. Device 10 will be anchored to the tissue of the septal defect by the physical interaction such as pressure from struts 22. The septal defect closure device may further comprise a plurality of tissue hooks located thereon to anchor the device in place in the septal defect.

The delivery and placement of device 10 in a septal defect is illustrated in FIGS. 5a and 5b, which depict placement of the device and removal of delivery catheter 40. Like FIG. 1, FIGS. 5a and 5b depict defects 6,6' of both atrial septal tissue and ventricular septal tissue, respectively.

The route by which the cardiac defects are accessed via catheter are described as follows. An ASD or VSD may be accessed from the arterial circuit, as shown in FIG. 5a. The catheter/device is introduced into the arterial vascular system and guided up the descending thoracic and/or abdominal aorta. The device may then be advanced into the left ventricle (LV) 50 through the aortic outflow tract. Once in LV 50, the device may be deployed in VSD 6'. Alternatively, once in LV 50, the device may be directed up through mitral valve 54 and into the left atrium (LA) 56. When the device is in LA 56, it may be directed into ASD 6 and installed. In FIG. 5b, device 10 is shown already in place in ASD 6 with catheter/delivery means 40 in the process of being withdrawn. Device 10' is shown being placed in VSD 6'. Device 10' is delivered to the area of septal defect 6' by catheter 40 and inserted in place, centered in septal defect 6' as shown in FIG. 5a. Device 10' may be either pulled or pushed out of catheter 40' and installed in a manner set forth more fully hereinbelow. After installation, device 10' will assume its preformed shape in a narrow center portion with enlarged ends. Device 10 is shown in place closing off atrial septal defect 6, as catheter delivery means 40 is being withdrawn.

Alternatively, an ASD or VSD may be accessed from the venous circuit, as shown in FIG. 5b. The catheter/device may be introduced into the venous system, advanced into Inferior Vena Cava (IVC) 62 or Superior Vera Cava (SVC) 64 and guided into the right atrium (RA) 60. The device may then be directed into ASD 6.

Alternatively, once in RA 60, device 10 may be advanced through tricuspid valve 66 into the right ventricle (RV) 58 and directed into VSD 6' and installed. In FIG. 5b, device 10 is shown being placed in ASD 6. Device 10' is shown already in place in VSD 6' with catheter 40' in the process of being withdrawn. Device 10 is delivered to the area of septal defect 6 by catheter 40 and inserted in place, centered in septal defect 6 as shown in FIG. 5b. Device 10 is shown in place closing off ventricular septal defect 6', as catheter delivery means 40' is being withdrawn.

Figure 6:
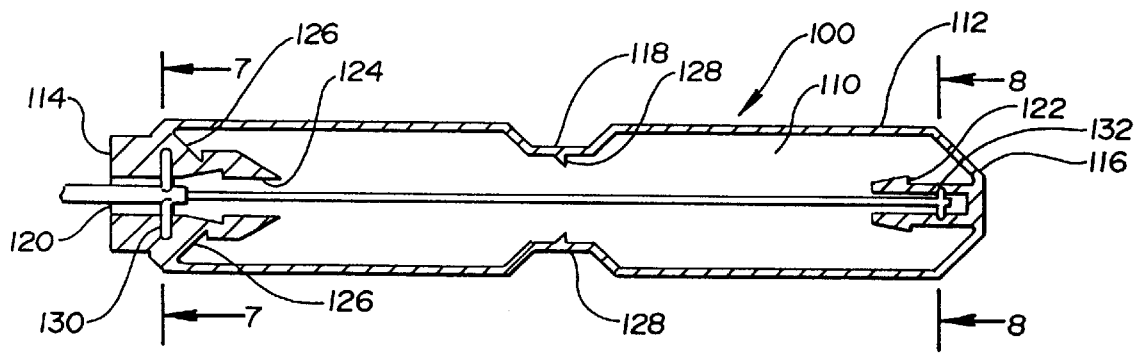
FIG. 6 is a sectional view of an alternative embodiment of a device according to the present invention.

An alternative embodiment is shown in FIGS. 6–10. FIG. 6 is a cross-section of the device, indicated generally at 100. Device 100 has an interior portion 110, an exterior portion 112, proximal and distal ends 114,116 and a center portion 118. Distal end 116 of device 100 is closed to block blood flow through its interior 110. Proximal end 114 has an opening 120 which provides access to interior 110. Arrow head 122 extends proximally from distal end 116 into interior 110. Lock 124 extends distally from opening 120 at proximal end 114 into interior 110, and is shaped to mate with arrow head 122. Arrow head 122 fits or snaps into lock 124 when distal end 116 is pulled toward proximal end 114. Lock 124 has a proximal undercut 126 shaped to mate with central barbs 128, which are located in the central portion 118 of interior 110. Proximal undercut 126 snaps onto central barbs 128 when proximal end 114 is pulled towards center 118.

Figure 7:
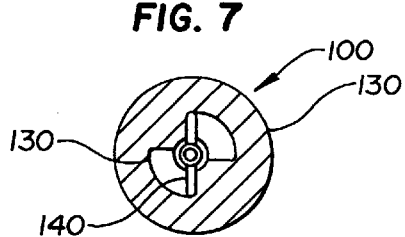
FIG. 7 is a sectional view thereof taken along line 7—7 in FIG. 6.
Figure 8:
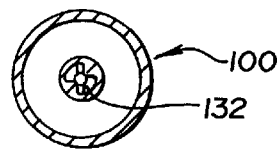
FIG. 8 is a sectional view thereof taken along line 8—8 in FIG. 6.
Figure 9:
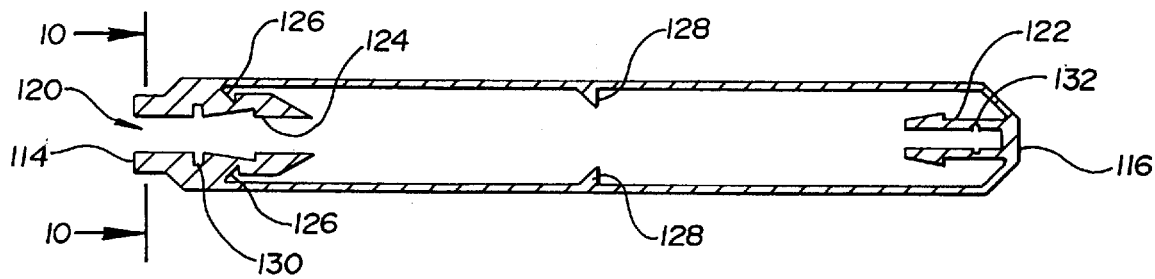
FIG. 9 is a view similar to that of FIG. 6 showing an alternative view thereof.
Figure 11:
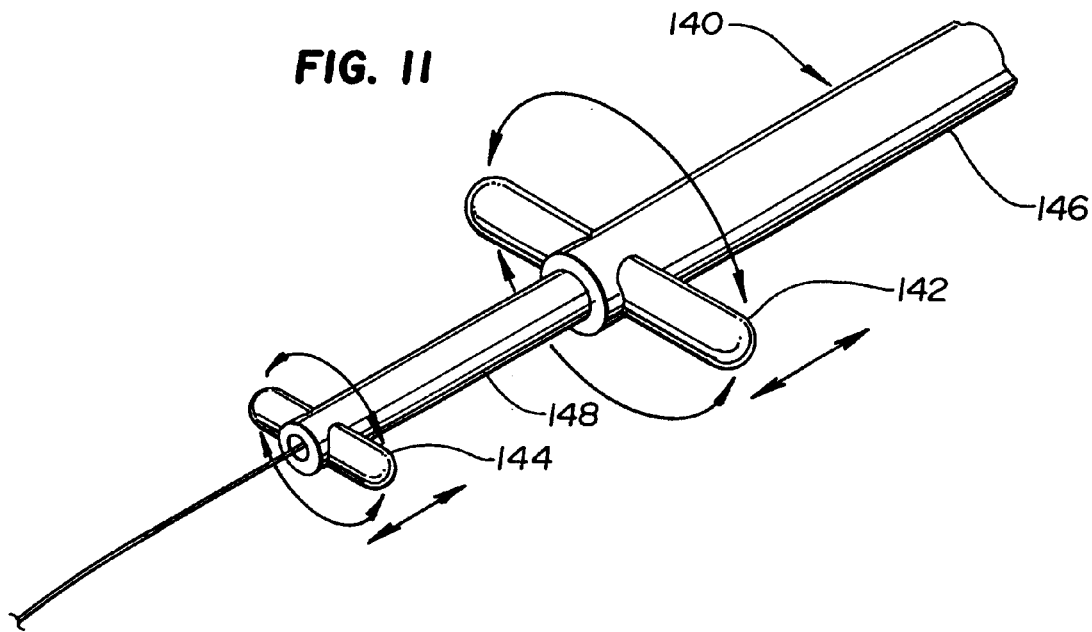
FIG. 11 is a perspective view of an intralumen mechanical mechanism thereof.
Figure 13:
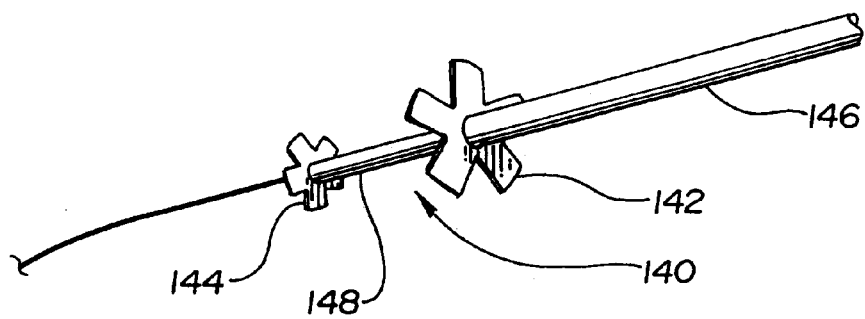
FIG. 13 is a perspective view of an alternative embodiment of the intralumen mechanical mechanism thereof.

Device 100 may be reversibly locked in place by means of an intralumen mechanical mechanism or twist-lok mechanism 140 (best seen at FIGS. 11 and 13). Both distal end 116 and proximal end 114 have twist-lok tracks, proximal 130 and distal 132. Cross sections of proximal twist-lok track 130 and distal twist-lok track 132 are shown at FIGS. 7 and 8, respectively. Proximal twist-lok track 130 is shown at FIG. 7 with twist-Lok mechanism 140 at resting/delivery position. Twist-lok mechanism 140 comprises a hollow outer shaft 146 with proximal twist-lok means 142 attached thereto and an inner shaft 148 having distal twist-lok means 144 attached thereto. As shown in FIG. 11, twist-lok means 142,144 may be T-shaped. Twist-lok means 142,144 may alternatively be star-shaped, as shown in FIG. 13. Twist-lok mechanism 140 may have twist-lok means of any other shape that will provide linear movement and permit locking and unlocking of the delivery means from device 100.

Twist-lok mechanism 140 is constructed and arranged to pull ends 114,116 toward center 118 of device 100. Alternatively, this movement may be reversibly effected through any suitable mechanical means, such as screws, ratchet, snap fittings, or tie off procedures, all of which would prevent the device from opening up and resuming a cylindrical shape.

Figure 12:
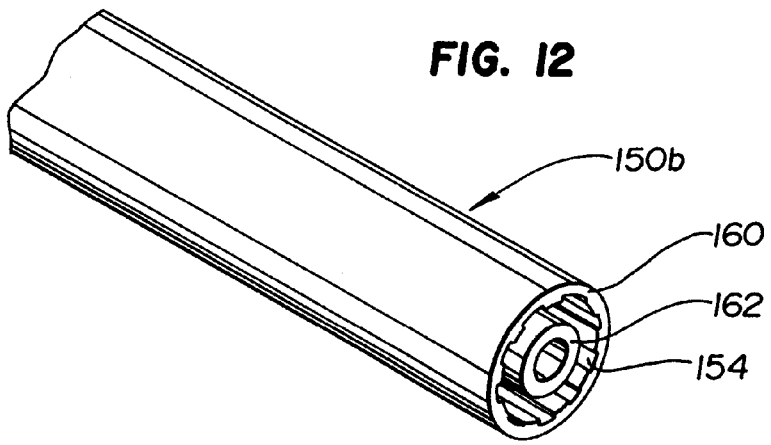
FIG. 12 is a perspective view thereof.

Referring to FIGS. 11–12, inner shaft 148 is rotatably mounted in outer shaft 146 to provide independent rotational movement of proximal and distal twist-lok means 142,144. Inner shaft 148 is also distally extensible from outer shaft 146.

In operation, proximal twist-lok means 142 is rotated counter-clockwise to its resting/delivery position, and is rotated clockwise to un-lock. Distal twist-lok track 132 of device 100 is shown at FIG. 8 with distal twist-lok means 144 therein. The rotational directions of proximal and distal twist-lok means 142, 144 are opposite of each other, so that device 100 may not detach from the delivery system unless twist-lok means 142,144 are rotated.

Subsequent removal of device 100 may be effected by inserting twist-lok mechanism 140 and rotating twist-lok means 142,144 in their respective removal directions to recapture device 100 for un-deployal and removal.

Figure 10:
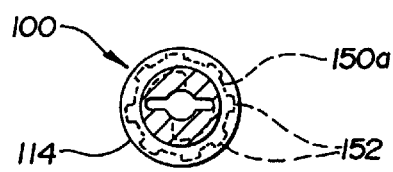
FIG. 10 is a sectional view thereof taken along line 10—10 in FIG. 9.

FIGS. 10 and 12 show an optional anchoring means 150a,150b which may be employed as a safety or reinforcement anchoring means 150a being located at the proximal end 114 of device 100, and anchoring means 150b being located at the distal end 160 of outer shaft 146 of twist-lok means 140. To eliminate rotation, splines 152 located at proximal end 114 of device 100 interlock or press fit into ribs 154 located in the interior of outer shaft 146 of twist-lok means 140. Distal movement of inner shaft 162 and shaft 148 will cause distal end 162 of inner shaft 148 of twist-lok means 140 to contact device 100, pushing anchoring means 150a of device 100 away from anchoring means 150b and out of outer shaft 146 of twist-lok means 140, disengaging splines 152. Proximal and distal twist-lok bars 142,144 are each capable of movement both distally and proximally depending on their current position, thus allowing for deploying and undeploying before releasing of device 100 altogether.

An alternative embodiment of the closure device according to the present invention is shown at FIGS. 14–17. FIG. 14 shows a perspective view of an alternative embodiment of a device according to the present invention. FIG. 15 shows a perspective view of a pull mechanism whereby the device is transformed into a plug. As shown in FIG. 14, the catheter delivered device, shown generally at 200, comprises a cylindrical shaft 212 having a proximal end 214, a distal end 216, and a central portion 218. Cylindrical shaft 212 has parallel struts 222. Struts 222 may be covered by a cloth or other suitable biocompatible covering.

Pull mechanism 230 comprises shaft 231 with distal pull bar (or twist-lok bar) 232, pull mechanism being constructed and arranged for insertion into device 200 through proximal opening 233 and distally through distal opening 234, and rotated, as shown at FIGS. 16–17. In the position shown at FIGS. 16–17, pull mechanism 230 can pull distal end 216 toward center 218 and center 218 toward proximal end 214. Alternatively this movement may be reversibly effected through any suitable mechanical means, such as screws, ratchet, snap fittings, or tie off procedures, all of which would prevent the device 200 from opening up and resuming a cylindrical shape.

As shown in FIGS. 16–17, hinge points 225 move radially away from the axis of the device in a hinge like fashion in response to the movement of proximal and distal ends 214, 216 toward the central portion 218 of the device 200. Hinge points 225 could be formed in a variety of ways. Such a hinge point could be a mechanical hinge, a thinned section created by chemical etching, mechanical denting, grinding, heat forming or machining, a weakened section created by micro cuts, tapered grooves, chemical treatment, or any other process which will cause a preferential stress point.

The embodiment shown in FIGS. 16–17 has three locking locations, center, proximal and distal. Distal end 216 may be locked to central portion 218 by means of distal locking pins 236 constructed and arranged to mate with central locking bores 240, and proximal end 214 may be locked to central portion 218 by means of central locking pins 242 constructed and arranged to mate with proximal locking bores 238. All mating locking surfaces are preferably shaped in such a manner to facilitate locking. Locking pins 236,242 may be ratcheted for the tightest fit. FIG. 17 is a partial view of device 200 showing the manner in which pins 236,242 respectively lock into bores 238,240.

Figure 18:
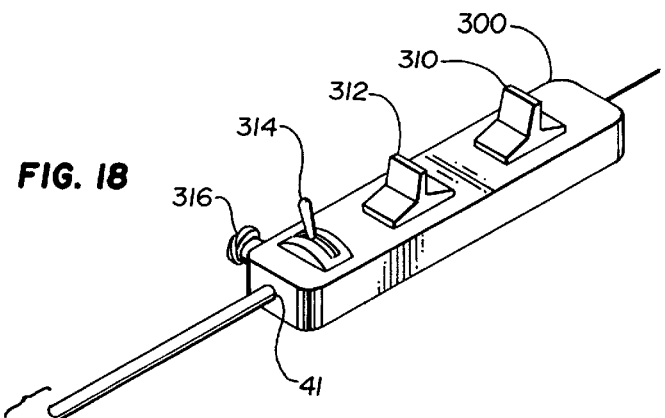
FIG. 18 is a perspective view of the invention with deployment catheter.
Figure 19:
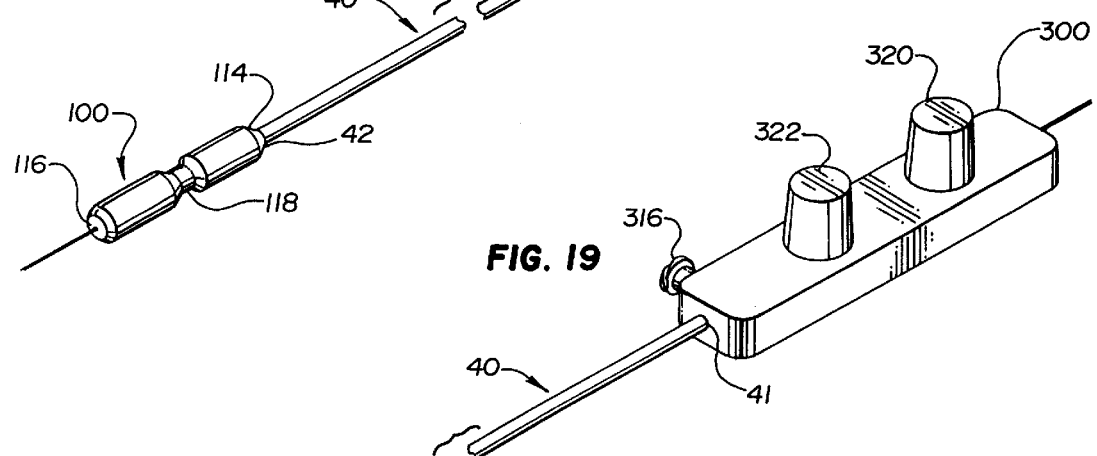
FIG. 19 is a perspective view of an alternative embodiment thereof.
Figure 20:
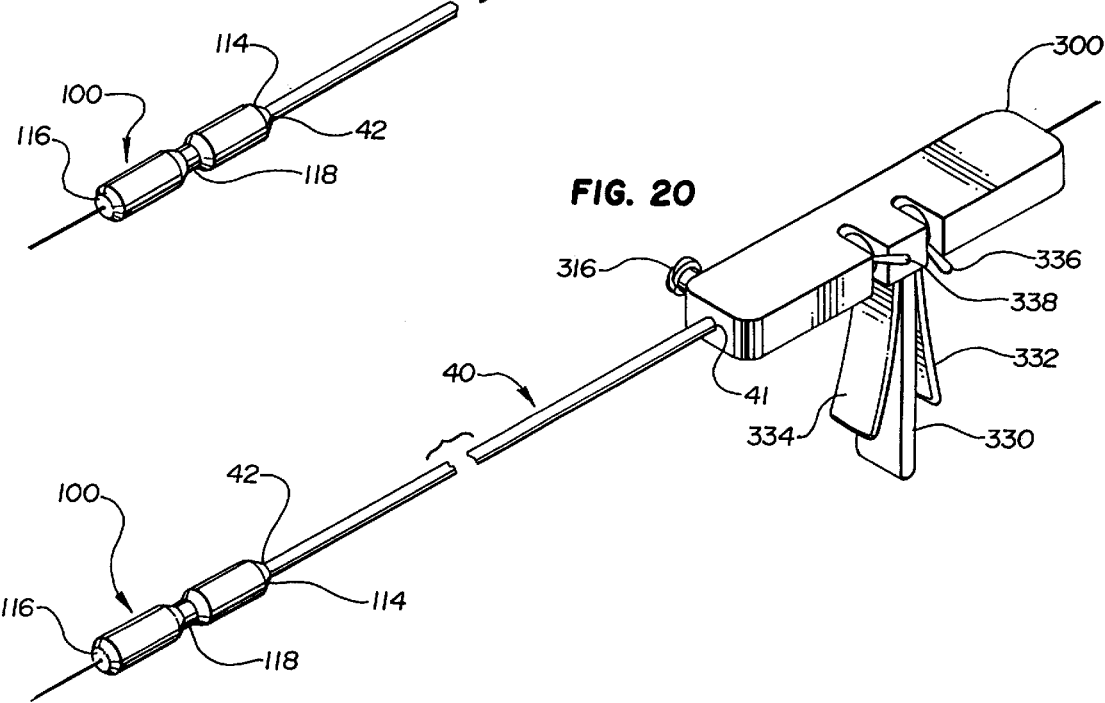
FIG. 20 is a perspective view of an alternative embodiment thereof.

FIGS. 18–20 show deployment catheters with device 100 as shown in FIG. 6. FIG. 18 shows deployment catheter 40 according to the present invention, with control means 300 located at proximal end 41 thereof. Control means 300 has linear slides 310,312, unlock lever 314 and flush port 316. FIG. 19 shows catheter 40 with an alternative embodiment of control means 300, having dual rotation knobs, i.e. proximal rotation knob 320 and distal rotation knob 322. FIG. 20 shows a further alternative embodiment of deployment catheter 40, having a gun-like handle 330 with up and down triggers 332,334, and un-lok slides 336,338.

The septal defect closure devices and apparatus disclosed herein may further comprise a plurality of tissue hooks located thereon to anchor the device in place in a septal defect. For example, FIGS. 21–22 show a sectional view of the device as in FIGS. 14, 16 and 17 further including a plurality of tissue hooks 270.

Figure 25:
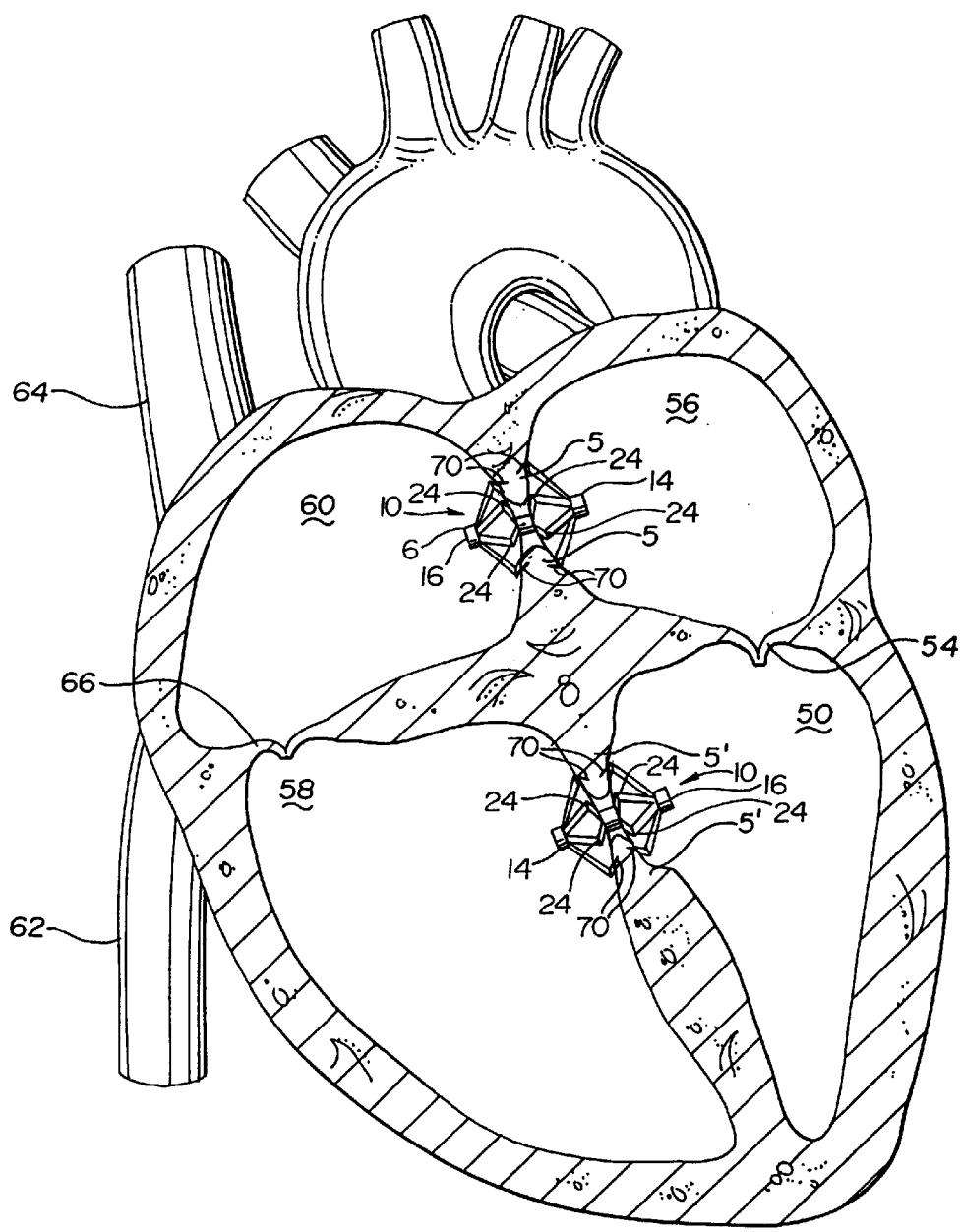
FIG. 25 is an anterior to posterior sectional view showing the septal defect closure device of FIGS. 23–24 after delivery to the atrial and ventricular defects as depicted therein.

FIGS. 23–24 show side views of a device as shown in FIGS. 3–4 respectively, the device further including a plurality of tissue hooks 70. FIG. 23 shows an intermediate conformation which the device would assume after delivery and during its mechanical transformation into a plug. FIG. 24 is a side view of the device as in FIG. 23 after its mechanical transformation into a plug. FIG. 25 is an anterior to posterior sectional view showing the septal defect closure device of FIGS. 23–24 after delivery to the atrial and ventricular defects as depicted therein. Device 10 is anchored to the tissue of the septal defect by the physical interaction of tissue hooks 70 therewith.

In a preferred embodiment, distal tip 42 of insertion catheter 40 according to the present invention is made of metal for visualization under fluoroscopy and is shaped in such a manner which does not interfere with the insertion of the twist-lok mechanism or pulling mechanism, fitting flushly with proximal end 14 of closure device 10.

The entire closure device or the portion thereof exposed to the heart chambers may be covered or coated with a fabric and/or elastic material (not shown) which may be biodegradable. This material will block blood shunting across the septal defect and may also allow tissue ingrowth to help in the stabilization of the device. Fabrics with which the mid-section may be coated with are polyamides, such as nylon 6, nylon 6,6, and the like, polyesters, such as PET, polyethers, fluorinated polymers, such as polytetrafluoroethylene, or biodegradable or nonbiodegradable fibers derived from natural sources such as carbohydrates, collagens, and proteins. The fabric may be of a woven knit, or solid structure.

The unique features of the device are the manner of its deployment and its reversibility, its low profile which may prevent interference with normal heart functions, the shape of the support struts, and the non-invasive nature of the delivery which would reduce costs normally associated with closure of such a defect. The device may be made of metal or polymeric material and is delivered via catheter in a non-invasive procedure. The device operates through mechanical means to close a septal defect.

The practice of the present invention achieves several objectives and advantages. The device and method of the present invention provides an advantage over surgery in that the cost of the procedure is substantially less, the risk of infection is less, the hospital residency time is less and there is no physically deforming scar.

Advantages include the flexibility of the reversible deployment, the fact that the non-invasive delivery would reduce costs associated with this type of procedure, the low profile may prevent interference with normal heart functions. Support arms have three support locations which may provide increased support arm strength.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, ii) a delivery catheter; and iii) an intralumen mechanical mechanism associated with the delivery catheter for remotely operating the closure device between the two configurations;

b) delivering the apparatus in the delivery configuration by means of the catheter to an area having an intravascular defect;

c) positioning the device in the defect;

d) operating the intralumen mechanical mechanism to cause the closure device to change from the delivery configuration to the plug configuration to thereby fit securely into the defect, and e) removing the catheter delivery means and intralumen mechanical mechanism.

2. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, ii) a delivery catheter; and iii) an intralumen mechanical mechanism associated with the delivery catheter for remotely operating the closure device between the two configurations;

b) delivering the apparatus in the delivery configuration by means of the catheter to an area having a defect;

c) positioning the device in the defect;

d) operating the intralumen mechanical mechanism, to cause the closure device to change from the delivery configuration to the plug configuration to thereby fit securely into the defect spanning both sides thereof;

e) removing the catheter delivery means and intralumen mechanical mechanism; and optionally f) reinserting and delivering a catheter and remotely operate intralumen mechanical mechanism to the area of the defect to operably contact the device;

g) operating the intralumen mechanical mechanism to change the device from the plug configuration to the delivery configuration;

h) repositioning the defect closure device in the defect; and i) operating the intralumen mechanical mechanism to cause the defect closure device to resume its plug configuration in the defect, again causing the defect to be reversibly closed/plugged, and j) removing the catheter delivery means and intralumen mechanical mechanism.

3. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, ii) a delivery catheter; and iii) an intralumen mechanical mechanism associated with the delivery catheter for remotely operating the closure device between the two configuration;

b) delivering the apparatus in the delivery configuration by means of the catheter to an area having a defect;

c) positioning the device in the defect;

d) operating the intralumen mechanical mechanism, to cause the closure device to change from the delivery configuration to the plug configuration to thereby fit securely into the defect spanning both sides thereof;

e) repositioning a catheter and remotely operable intralumen mechanical mechanism to the area of the defect to operably contact the device;

f) operating the intralumen mechanical mechanism to change the device from the plug configuration to the delivery configuration, and g) removing the catheter, intralumen mechanical mechanism and the defect closure device from the defect.

4. A method of reversibly closing an intravascular defect in a body, the method comprising the steps of:

a) providing an apparatus for reversibly closing an intravascular defect in a body, the apparatus comprising:

i) a reversibly configured defect closure device that is unitary in construction and comprises a first end, a second end, a center portion and having a delivery configuration and a plug configuration, the device also including a cylindrical shaft having an axis therethrough and a plurality of cuts therethrough parallel to the axis;

ii) a catheter delivery means; and iii) an intralumen mechanical mechanism located in the catheter delivery means for operating the closure device between the two configurations;

b) delivering the apparatus to an area having a defect;

c) positioning the center portion of the shaft of the device in the defect;

d) pulling the shaft in a proximal direction relative to the catheter by means of the intralumen mechanical mechanism, thereby creating at least two flattened support struts which move radially away from the axis in a hinge like fashion causing the closure device to plug the defect;

e) removing the catheter delivery means and intralumen mechanical mechanism; and optionally at a later time;

f) inserting and positioning a catheter and intralumen mechanical mechanism at the area of the defect in operable contact with the defect closure device;

g) removing the defect closure device from the defect by moving the struts of the defect closure device radially toward the axis by means of the intralumen mechanical mechanism thereby causing the defect closure device to approach or resume its delivery configuration; and h) withdrawing the apparatus and device from the body.

5. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, the device further comprising an elongate shaft having an axis therethrough and a plurality of concentric parallel cuts therethrough;

ii) a delivery catheter; and iii) an intralumen mechanical mechanism associated with the catheter for operating the closure device between the two configurations;

b) delivering the apparatus in the delivery configuration to an area having a defect by means of the catheter;

c) inserting the shaft of the device through the defect and positioning it therein;

d) pulling on the shaft by means of the intralumen mechanical mechanism, causing the closure device to assume the plug configuration and plug the defect;

e) removing the catheter and intralumen mechanical mechanism;

f) reinserting a catheter and intralumen mechanical mechanism to the area of the defect and operably contacting the device;

g) operating the intralumen mechanism to reconfigure the device to the delivery configuration and removing the defect closure device from the defect;

h) repositioning the defect closure device in the defect; and i) causing the defect closure device to resume its plug configuration by operation of the intralumen mechanism again causing the defect to be reversibly plugged; and j) removing the catheter and intralumen mechanical mechanism.

6. A method of reversibly closing an intravascular defect in a body, the method comprising the steps of:

a) providing an apparatus for closing a defect in a body, the apparatus comprising:

i) a reversibly deformable defect closure device that is unitary in construction and comprises a first end, a second end, a center portion and having a delivery configuration and a plug configuration, the device including a cylindrical shaft having an axis therethrough and a plurality of cuts therethrough parallel to the axis;

ii) a catheter delivery means; and iii) an intralumen mechanical mechanism associated with the catheter for deforming the closure device between the two configurations;

b) delivering the apparatus to an area having a defect;

c) positioning the center portion of the shaft of the device in the defect;

d) pulling the first and second ends of the shaft toward the center portion thereof, by means of the intralumen mechanical mechanism thereby forming at least two flattened support members which move radially away from the axis in a hinge like fashion causing the closure device to assume the plug configuration and plug the defect;

e) removing the catheter delivery means and intralumen mechanical mechanism; and optionally at a later time f) inserting and delivering a catheter and intralumen mechanical mechanism to the area of the defect to operably contact the device;

g) removing the defect closure device from the defect by operating the intralumen mechanical mechanism to deform the device thereby causing the device to resume its delivery configuration; and h) withdrawing the apparatus and device from the body.

7. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, ii) a delivery catheter; and iii) an intralumen mechanical mechanism associated with the delivery catheter for remotely operating the closure device between the two configurations;

b) delivering the apparatus in the delivery configuration by means of the catheter to an area having a defect;

c) positioning the device in the defect;

d) operating the intralumen mechanical mechanism, to cause the closure device to change from the delivery configuration to the plug configuration to thereby fit securely into the defect spanning both sides thereof;

e) operating the intralumen mechanical mechanism to change the device from the plug configuration to the delivery configuration; and f) removing the catheter, intralumen mechanical mechanism and the defect closure device from the defect.

8. A method of closing an intravascular defect in a body, the method comprising the steps of:

a) providing an apparatus for closing an intravascular defect in a body, the apparatus comprising:

i) a reversibly configured defect closure device that comprises a first end, a second end, a center portion and having a delivery configuration and a plug configuration, ii) a delivery catheter; and iii) an intralumen mechanical mechanism associated with the delivery catheter for remotely operating the closure device between the two configurations;

b) delivering the apparatus in the delivery configuration by means of the catheter to an area having a defect;

c) positioning the device in the defect;

d) operating the intralumen mechanical mechanism, to cause the closure device to change from the delivery configuration to the plug configuration to thereby fit securely into the defect spanning both sides thereof;

e) operating the intralumen mechanical mechanism to change the device from the plug configuration to the delivery configuration;

f) repositioning the defect closure device in the defect;

g) operating the intralumen mechanical mechanism, to cause the closure device to change from the delivery configuration to the plug configuration to thereby fit securely into the defect spanning both sides thereof;

h) operating the intralumen mechanical mechanism to change the device from the plug configuration to the delivery configuration; and f) removing the catheter, intralumen mechanical mechanism and the defect closure device from the defect.

* * * * *

UNITED STATES PATENT AND TRADEMARK OFFICE
CERTIFICATE OF CORRECTION

PATENT NO. : 6,024,756

DATED : February 15, 2000

INVENTOR(S) : Joseph Huebsch; Paul J. Buscemi; Thomas J. Holman; Danny J. Langanki It is certified that an error appears in the above-identified patent and that said Letters Patent is hereby corrected as shown below:

Column 12, Line 41: delete "f)", insert -- i) --

Signed and Sealed this

Third Day of April, 2001

*Attest:*

NICHOLAS P. GODICI

*Attesting Officer*     *Acting Director of the United States Patent and Trademark Office*